United States Patent [19]
Tuzzeo et al.

[11] 3,987,670
[45] Oct. 26, 1976

[54] BLADE WEAR MEASURING SYSTEM

[75] Inventors: James J. Tuzzeo, Columbus, Ohio;
Donald F. Aitken, Jr., Plainville, Conn.

[73] Assignee: General Electric Company, Columbus, Ohio

[22] Filed: May 15, 1975

[21] Appl. No.: 577,761

[52] U.S. Cl. ................................................ 73/104
[51] Int. Cl.² ......................................... G01N 3/56
[58] Field of Search ............... 73/104, 7; 33/DIG. 5, 33/143 L, 147 N, 169 B

[56] References Cited
UNITED STATES PATENTS

| | | |
|---|---|---|
| 2,578,869 | 12/1951 | Washburn ........................ 33/143 L |
| 2,583,791 | 1/1952 | Neff ............................ 33/147 N UX |
| 3,645,002 | 2/1972 | Hefti ............................. 33/169 B X |
| 3,763,698 | 10/1973 | Sazuki et al. ........................ 73/88 R |
| 3,803,906 | 4/1974 | Ross ................................. 73/88 R X |

*Primary Examiner*—Jerry W. Myracle
*Attorney, Agent, or Firm*—Donald J. Voss; Granville M. Pine; Edward A. Hedman

[57] ABSTRACT

A displacement transducer is manually applied to the cutting surface of a diamond wheel to measure the fixed reference distance and thus degree of wheel wear. The output of the transducer is amplified and directed to visual or print out devices, and archival systems. The transducer signal may be transmitted to provide central processing of field measurements.

4 Claims, 3 Drawing Figures

BLADE WEAR MEASURING SYSTEM

BACKGROUND OF THE INVENTION

The present invention relates to measurement system and more particularly to an elecromechanical system for blade wear measurements.

Abrasive saw blades, such as diamond grit blades, are required to cut a wide variety of materials which vary in density, hardness grain size, etc. In addition, the characteristics of the diamond blade vary depending upon the crystal size, bonding material etc. These combinations of factors contribute to affect the cost of cutting, e.g. blade wear, cutting rate, removal rate, etc.

To determine the optimum conditions for blade operations, certain parameters must be measured. One of the primary parameters is blade wear. Diamond blades are generally in the range of about 18-36 inches in diameter and present distinct problems when attempts are made to measure wear. The wheel may have a continuous abrasive around its periphery or the abrasive may be segmented with gaps between the segments.

PRIOR ART

The known prior art method of measuring blade wear consists of the use of precision micrometers. The most popular method involves removal of the blade from the spindle of the machine. The blade is positioned by means of the arbor hole in its center on a fixture to which is fastened a precision micrometer. The measure of blade wear is accomplished manually, see e.g. M. W. Hinshaw, Test Procedures For Evaluating Diamond Circular Saw Blades Cutting Non-metallic Materials, Industrial Diamond Review, 107–114 (March 1969).

Two major sources of error in prior methods are due to (1) the variation in the extent to which the technician tightens down on the micrometer head — this can be even more critical if different technicians make measurements during any one test — and (2) the differences in the dimensions between the spindle shaft of the machine and spindle shaft of the blade measuring device. The error produced by the latter can be accentuated by the minor variation in the arbor hole sizes for blades produced by the different blade manufacturers.

There have been methods which do not necessitate removal of the blade from the machine to measure blade wear, but these methods also involve manual techniques with precision micrometers. In addition, this involves indenting or drilling holes in the blade center to accurately position the measuring device. Indenting or drilling of holes in the blade center can lead premature loss in tension of the blade or complete inability to adequately tension the blade. The importance and difficulties of proper blade tensioning increases as blade diameter increases.

SUMMARY OF THE INVENTION

The present invention overcomes the problems of the prior art micrometer methods by utilizing a displacement transducer coupled to suitable readout devices to accurately and precisely determine the wear of a blade.

DETAILED DESCRIPTION OF A PREFERRED EMBODIMENT

Figure 1:
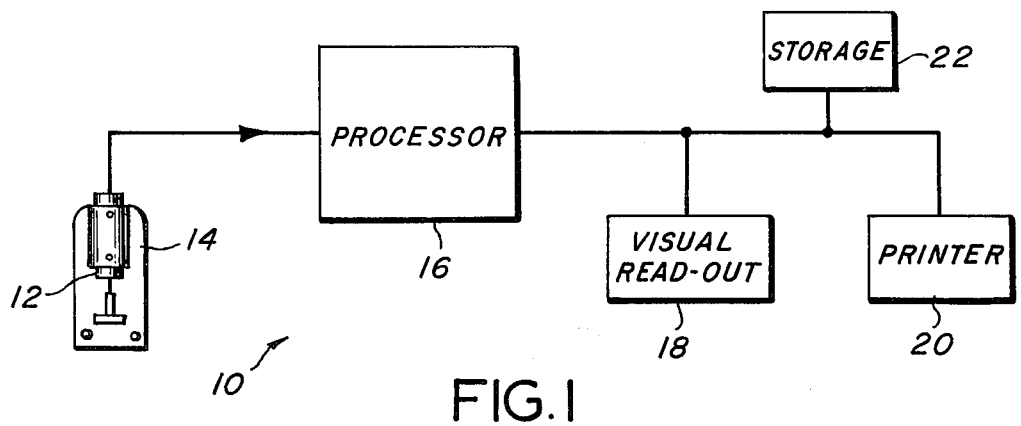
FIG. 1 is a schematic view illustrating the components of a blade wear measuring system in accordance with the present invention.

While this invention is susceptible of embodiment in many different forms, there is shown in the drawings and will hereinafter be described in detail a preferred embodiment of the invention, with the understanding that the present disclosure is to be considered as an exemplification of the principles of the invention and is not intended to limit the invention to the embodiment illustrated.

FIG. 1 illustrates a blade wear measuring system 10 in accordance with the present invention. System 10 includes a displacement transducer 12 mounted on a portable fixture 14. The electrical signal generated by transducer 12 is processed, as described below, in a process system 16. The processed signal is then directed to any one of several output devices including a visual readout device 18, a printer 20, or an archival retrieval system 22.

Transducer 12 is of the displacement type and may operate on the piezo-electric effect or as a linear potentiometer. Suitable transducers are commercially available, e.g. Model No. 243-000, sold by Transducer Technology, Inc. Ellington, Conn.

Figure 2:
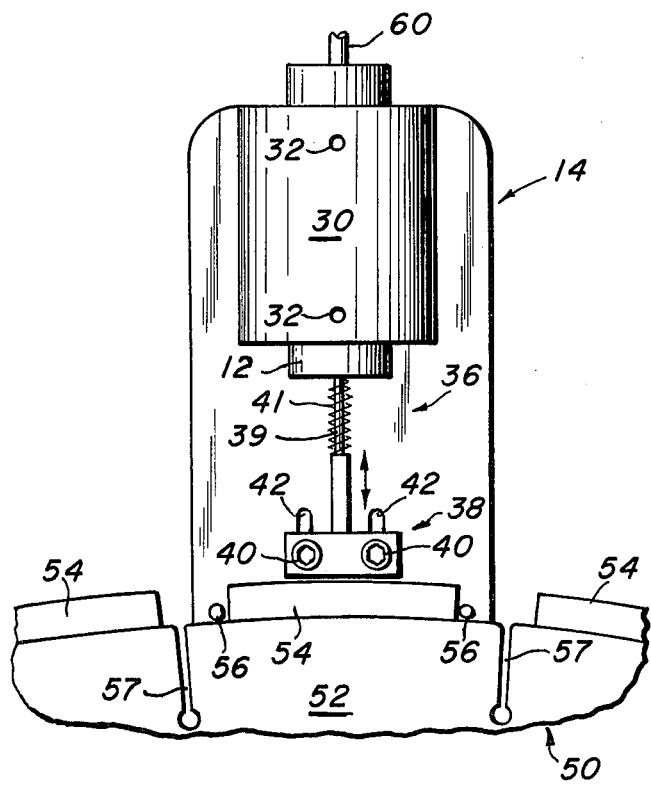
FIGS. 2 and 3 are front and side elevation views, respectively, partly fragmentary, illustrating a measuring fixture for segment blade wheels.
Figure 3:
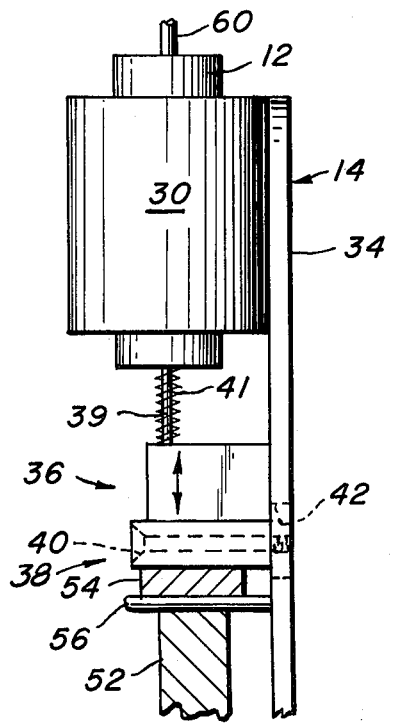

Referring to FIGS. 2 and 3, transducer 12 is generally cylindrical in shape and positioned coaxially within a mounting collar 30 by radially disposed fasteners 32. Collar 30 is attached to a fixture plate 34 as by welding.

Extending from the lower end of transducer 12 is a follower assembly 36, which includes an inverted T-shaped follower 38 attached to the end of transducer rod 39. It will be appreciated that movement of rod 39 results in the generation of an electrical signal proportional to the extent of movement.

Follower 38 includes a pair of spaced-apart slide pins 40, which slide in slots 42 in fixture plate 34 to assure that only unidirectional movement is transmitted to transducer 12. Follower 38 is normally based outwardly of transducer 12 by compression spring 41 positioned coaxially about rod 39 and abutting the transducer and follower.

As illustrated, the transducer fixture is arranged for use in measuring the wear of a circular, segment type diamond blade 50. This type of blade includes a circular hub 52 which has a plurality of segment shaped diamond abrasive elements 54 positioned at spaced locations about the periphery of hub 52. Other type of circular blades, as well as straight blades may also be used with modifications to the fixture 14.

A fixed reference datum is required for measuring the extent of wear. To this end, a pair of pins 56 extend from plate 34. Pins 56 are spaced at sufficient distance apart to bridge the diamond segment 54 and rest on the periphery of hub 52, or in slots 57 in hub 52.

Fixture 14 is sized to be manually graspable and, when positioned as shown in FIG. 2, transducer 12 generates a signal proportional to the displacement of the follower from a reference datum. It is sometimes preferable to set the reference datum as the abrasive thickness prior to any wear so that further measurement results in direct wear data.

The signal generated by transducer 12 is carried by cable 60 to the processor unit which includes an amplifier and scale factor (calibration coefficient) circuitry.

The processor unit also includes means for storing the reference datum and means for subtracting the reference data from the measured data to provide net wear measurement. The present invention is particularly adapted for field measurements and may be used for remote measurement central processing. To this end, processor system 16 would be in two parts. The first part being a transmitter portable with the transducer and a receiver and associated circuitry located at the processing point. This type of system is particularly useful in gathering data in rock quarries, where only a transducer and transmitter need be carried to the blade for measurement and the data is transmitted back to a receiver and remaining equipment on a truck.

After the signal has been processed it is outputted through appropriate devices discussed above.

It will be appreciated that present invention provides a fast and thus economical apparatus for measuring blade wear and thus provide the necessary intelligence data needed for the proper management of abrasive tools.

What is claimed is:

1. A system for measuring blade wear comprising: a displacement transducer having a follower, said transducer being adapted and arranged to generate a signal output in response to displacement of the follower; fixture means for mounting said transducer in fixed relative position thereon, said fixture means having fixedly positioned reference means for engaging said blade on a predetermined location such that said follower contacts the wear surface of the blade; processing means operatively coupled to said transducer means to derive a signal input therefrom and amplify and calibrate said signal and said processing means also including means for storing reference datum and means for subtracting said reference datum from the data measued by the transducer to provide a net blade wear output signal; and means coupled to said processing means for outputting the net blade wear signal.

2. The system of claim 1, wherein said processing means includes means adjacent said transducer for transmitting said transducer signal, and receiver means, remote from transducer, for receiving said signal, whereby remotely measured, centrally processed blade wear intelligence may be gathered.

3. The system of claim 1, wherein said output means includes a visual readout.

4. The system of claim 1, wherein said output means includes a printer.

* * * * *